United States Patent [19]

Lataix

[11] Patent Number: 5,453,096
[45] Date of Patent: * Sep. 26, 1995

[54] DEVICE FOR THE DISTRIBUTION OF SUCCESSIVE DOSES OF A FLUID PRODUCT-IN PARTICULAR MEDICINAL OR COSMETIC-CONTAINED IN A VIAL

[75] Inventor: Gilbert Lataix, Clermont-Ferrand, France

[73] Assignee: Merck & Co., Inc., Rahway, N.J.

[*] Notice: The portion of the term of this patent subsequent to Feb. 21, 2012 has been disclaimed.

[21] Appl. No.: 97,633

[22] Filed: Jul. 26, 1993

[51] Int. Cl.$^6$ ............................................. A61M 5/00
[52] U.S. Cl. ......................................... 604/246; 604/68
[58] Field of Search .................... 604/63, 68, 71, 604/82, 85, 246, 256, 257; 222/30

[56] References Cited

U.S. PATENT DOCUMENTS

| | | | |
|---|---|---|---|
| 4,261,356 | 4/1981 | Turner et al. | 604/246 |
| 4,262,668 | 4/1981 | Schmidt | 604/246 |
| 4,267,836 | 5/1981 | Whitney et al. | 604/246 |
| 4,626,242 | 12/1986 | Fejes et al. | 604/68 |
| 4,642,095 | 2/1987 | Dettbarn et al. | 604/68 |
| 4,699,615 | 10/1987 | Fischell et al. | 604/246 |
| 4,739,770 | 4/1988 | Stephens et al. | 604/246 |
| 4,792,334 | 12/1988 | Py | 640/301 |
| 4,913,699 | 4/1990 | Parsons | 604/68 |
| 4,946,452 | 8/1990 | Py | 640/301 |
| 4,995,864 | 2/1991 | Bartholomew | 604/246 |
| 5,061,243 | 10/1991 | Windchell et al. | 604/246 |
| 5,390,822 | 2/1995 | Lataix | 222/30 |

FOREIGN PATENT DOCUMENTS

0437953A1  7/1991  European Pat. Off. .......... A61F/9/00

*Primary Examiner*—C. Fred Rosenbaum
*Assistant Examiner*—Chalin Smith
*Attorney, Agent, or Firm*—Francis P. Bigley; Mark R. Daniel

[57] ABSTRACT

The device comprises a receiving housing for receiving and maintaining the vial, this latter being comprised of a pocket (10) containing the product and a nozzle (11) in which is inserted a pump (8) which has a variable volume chamber (8000) controlled by a movable actuating member (85); the device according to the invention comprises a pushing means (42) capable of acting against this actuating member (85) through the wall of the casing so as to displace it in a so-called "forward" direction against a resilient release means, a locking means (46) capable of locking the pushing means (42) in a position in which it maintains the actuating member in a mobile state at the end of the "forward" stroke, and an unlocking control means (52) of said locking means (46).

Device for distributing successive and precise doses of a fluid product, in particular medicinal or cosmetic, for instance for the instillation of an eye lotion.

2 Claims, 10 Drawing Sheets

FIG.3

FIG_11

FIG_15

FIG_16

FIG_17

FIG_18

DEVICE FOR THE DISTRIBUTION OF SUCCESSIVE DOSES OF A FLUID PRODUCT-IN PARTICULAR MEDICINAL OR COSMETIC-CONTAINED IN A VIAL

BACKGROUND AND SUMMARY OF THE INVENTION

The present invention is directed to a device for use in the distribution of successive doses of a fluid product—in particular medicinal or cosmetic—contained in a vial, and more precisely in a vial of the type containing a flexible casing mounted on a rigid support and comprised of a thin wall, flexible air-tight pocket containing the fluid, and of a tubular nozzle for the distribution of the product, said nozzle being connected to a pump which is inserted in the tubular nozzle within the casing; the pump is provided with a variable volume chamber and is equipped with a movable actuating member which can be operated from the outside of the casing thanks to the distortable nature of the pocket. Its movement in a given direction, hereinafter called "forward direction" results in the aspiration of a certain quantity of product from the pocket inside the chamber, whereas its movement in the reverse direction, hereinafter called the "backward direction" results in the delivery of a determined dose of the product (previously aspired) outside said chamber, so that the dose of product is expelled from the vial through the tubular nozzle. It thus comes out of the nozzle in the form of a jet. Furthermore, a resilient release means is provided, which normally acts on the actuating member in the "backward" direction.

The word "fluid product" is intended throughout this specification and claims, to mean any pasty or liquid substance which is capable of conforming the shape of the device containing it, and capable of being expelled from this latter under the form of a jet, whether continuous or made up of individual drops.

A packaging vial having the hereinbefore described features, and a process for manufacturing thereof are the object of a patent application U.S. Ser. No. 08/077,635, filed Jul. 26, 1993, now U.S. Pat. No. 5,390,822 which has been simultaneously filed. The vial is more particularly (but not exclusively) aimed at containing an eye lotion.

The pocket has an elongated shape of which the major axis substantially extends the axis of the tubular nozzle, the bottom of this pocket, which is located at the opposite end of the nozzle, being closed by soldering.

The rigid support includes a cartridge made out of plastic material, provided with a bracket for retaining the nozzle and a pair of centering legs between which the pocket is made fit.

The cartridge comprises means for counting the number of distributed doses, said counting means include two free-rotating gears located near one another of which the first is designed to turn a fraction of a turn each time that a dose of the product is delivered and it is designed to turn the second gear a fraction of a ram, by using an actuating leg, each time it goes completely around; one of the teeth of the second gear is shaped in such a way that it prohibits movement to be continued after a complete turn (minus one tooth) of this second gear.

In a first embodiment of the vial which is the object of the simultaneous Patent Application U.S. Ser. No. 08/097,635, filed Jul. 26, 1993, now U.S. Pat. No., 5,390822 mentioned earlier, which is illustrated in FIG. 1 thereof, the nozzle has a general shape of revolution, while the pump body also has at least one portion with the general shape of a revolution fitted into the nozzle, coaxially with the latter, this portion showing an annular shoulder providing its connection in axial direction with the wall of the nozzle; the actuating member of the pump is moveable in translation according to the axis of the nozzle and of the pump body, and has an annular base providing its connection in axial direction with the wall of the nozzle near the connecting zone of the latter with the pocket, while, in its portion separating the shoulder from the base, the wall of the nozzle forms an axially distortable bellow.

Figure 20:
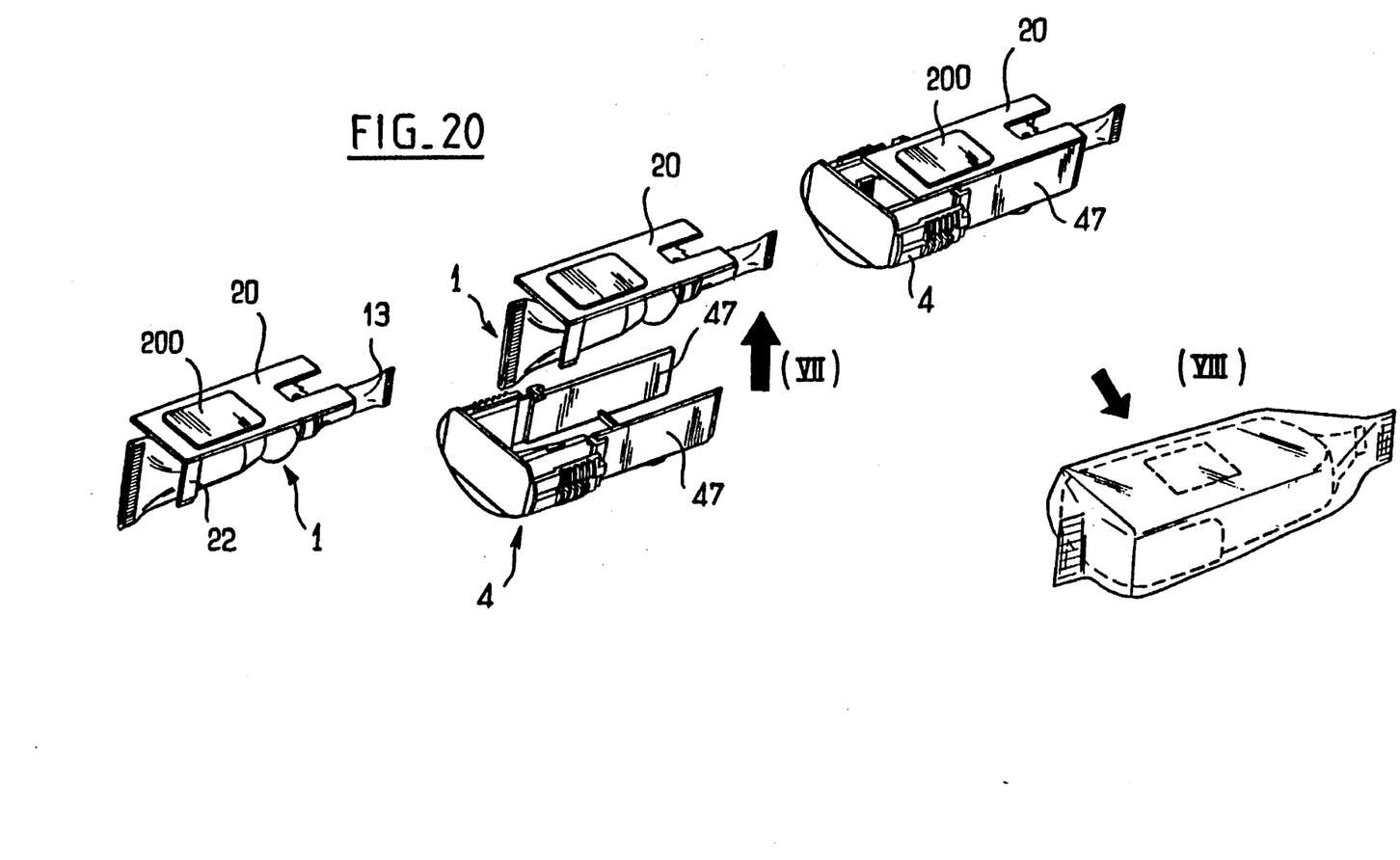
FIG. 20 is a perspective schematic view illustrating the assembly and conditioning of a vial in a drawer which is part of the device.
Figure 21:
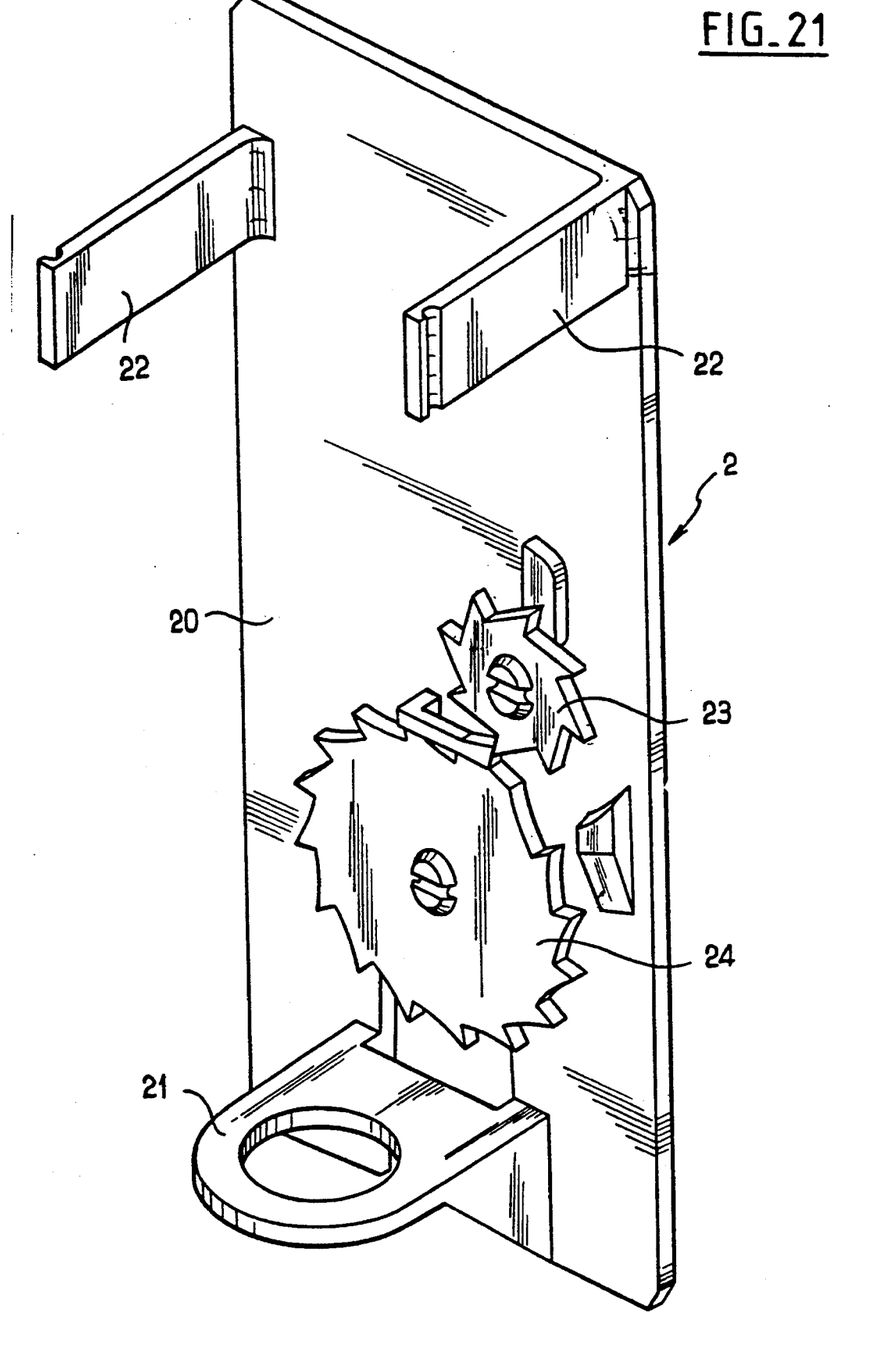
FIG. 21 is a perspective view of the rigid support which is part of the vial.

In a second embodiment, illustrated FIG. 20 of this Application, the pump body shows a part which is set at a fight angle in relation to the portion fitted into the nozzle and which serves to guide the actuating member in translation. In·this case, the actuating member of the pump is moveable in translation according to an axis which is perpendicular to the major axis of the pocket. The pump body shows a part which is set at a right angle in relation to the portion fitted into the nozzle and which serves to guide the actuating member in translation. This latter has the general shape of a socket which shows a cylindrical part with a closed bottom forming a cylinder, while said part set at a right angle in relation to the pump body includes a tubular cylindrical sleeve forming a piston, which fits into this cylindrical portion. Its is thus the inside of the sleeve and the inside of the cylindrical part define the above-mentioned variable volume chamber. The resilient means consists in a compression spring which has an action on the socket for the lowering of the piston in the cylinder (i.e. in the delivery direction).

This invention is related to a device which enables the use of a vial for the distribution of the product in the form of successive doses, having a well determined volume, for instance for the instilhation of an eye lotion in the eye when dealing with a packaging vial for an eye lotion.

An object of this invention is to provide a device which can be used easily and safely by unskilled people, especially elderly patients.

Another object of this invention is to provide a device, the design of which permits its manufacturing on a large or even very large scale, at a low manufacturing cost.

Another object of this invention is to provide a device having a small bulk and which is susceptible of being carded (along with its vial) in the pocket of a piece of cloth.

Yet another object of this invention is to provide a device which distributes very precise doses, at the beginning as well as at the end of the use (when the vial is almost empty).

Another object of this invention is to provide a device in which the vial, even when it has already been used, is appropriately protected from the external environment, whether mechanically (against shocks) or at the level of hygiene (against contaminations).

Last, when applied to the instillation of an eye lotion, a major object is that the actuating of the device can be achieved in a smooth way by the patient himself, this action not creating disturbing pressure against his eyeball.

Another object of this invention, still in connection with this application, is to provide a device equipped with the appropriate means for lowering the eyelid before and during instillation, in the region of the eye cul-de-sac, in order to expose this region in an appropriate manner to the jet of product which is expelled from the vial.

It should be noted that it has already been suggested to provide an eye lotion instillation device with a moveable eyelid lowering member, actuated during instillation (see EP-A-0 437 953). Such means are already known per se.

These objectives are achieved, in accordance with the invention, by means of a device comprising:

a receiving housing used for receiving and maintaining the vial in view of the distribution of the product;

a pushing means capable of actuating against said moveable actuating member through the wall of the casing in order to displace it in the "forward" direction, against said resilient release means;

a locking means capable of locking said pushing means in a position in which it maintains the moveable actuating means at the end of its "forward" stroke;

a control means for unlocking said locking means.

Furthermore, a certain number of advantageous, yet non limiting, features are as follows:

the pushing means is moveable according to a direction which is almost perpendicular with the axis of the nozzle;

the pushing means is supported by an articulated tab which is integral with the housing;

the locking means is a fixing nose for said tab;

the device comprises a plunger which can be grasped by the user and which is moveable in translation according to the axis of the housing;

this plunger has a generally tubular shape and surrounds the housing;

this plunger is provided with a rail acting against the pushing means in the so-called "forward" direction when it is moved in a certain direction;

this plunger is provided with a stopping means which acts against the blocking means in the unlocking direction, when it is moved in a reverse direction.

In a preferred embodiment, this device is intended for the instillation, in the eye of a patient, of an eye lotion contained in the vial. In this case, said housing is advantageously provided, at one of its ends, on the nozzle side, with a fitting made of a flexible material, which comprises an eyepiece, the central part of which shows an aperture positioned opposite the free end of the nozzle, the contour of which is conformed to match with the contour of the eyeball of the user.

In a particularly advantageous embodiment, this flexible fitting comprises an articulated eyelid lowering member.

The movement of this eyelid lowering member can be obtained easily, by means of a control device which is actuated by the plunger.

Furthermore, according to a certain number of additional features:

this control device comprises a shutter capable of positioning itself behind and opposite the aperture of the eyepiece when the eyelid lowering member is not used, and to retract itself in use;

when the rigid support comprises a cartridge provided with counting means of the distributed doses, the plunger is integral with a finger actuating said counting means;

the device comprises a closing lid (hood) which can adapt itself on the receiving housing, on the nozzle side, and which prevents the plunger from moving.

Other features and advantages of the present invention will appear from the description and the appended drawings which present a preferred embodiment thereof.

DETAILED DESCRIPTION OF THE INVENTION

Figures 1, 2:
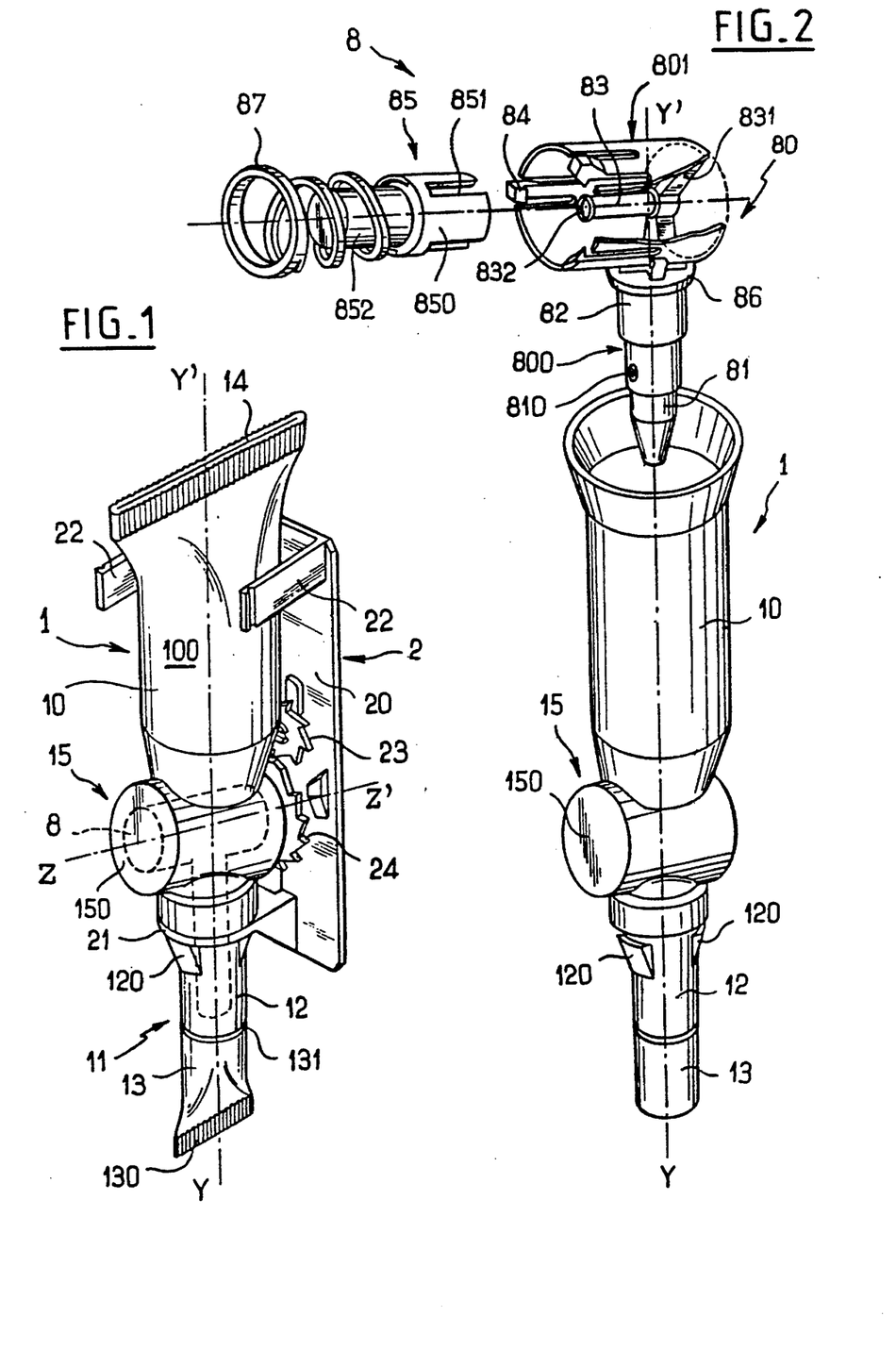
FIG. 1 is a general perspective view of a vial which can be used with the device of the invention.
FIG. 2 is an exploded perspective view of the casing making up the vial of FIG. 1, before it is filled up, and of the pump with which the vial is equipped.

The vial illustrated FIG. 1 is similar to that which is the object of the second embodiment (FIGS. 20 to 21) of the simultaneous Patent Application mentioned earlier.

It comprises a flexible casing 1, a rigid support 2 and a pump 8.

These three elements are made of synthetic material.

The material of casing 1 is a highly flexible and distortable elastomeric material (synthetic robber). The material which makes up support 2 and pump 8 is a more rigid plastic material, for instance polyethylene.

A fluid product 100 (liquid or pasty), in this case an eye lotion, is contained in the casing.

Casing 1 comprises a pocket 10 containing the product and a tubular nozzle 11 which is used for the distribution of the product. These two parts are manufactured in one element, by moulding. Pocket 10 has an elongated shape and one, 14, of its ends which constitutes its bottom part, is closed by pressing and soldering, for instance heat soldering. At the level of its central part, the pocket has an oval or circular section. At the other end, nozzle 11 has the shape of a revolution and the YY' axis of the nozzle corresponds to the major axis of the elongated pocket. Nozzle 11 is tubular. Its free end, which is located opposite pocket 10, is closed by an obturating element 13. This obturating element is a sleeve which prolongates the end part 12 of the nozzle and which is an integral part thereof. This sleeve has a pressed, then heat soldered end.

Element 13 can be easily detached from the nozzle via a less resistant groove 131.

According to an important feature of this type of vial, a pump 8 which is used for dosing and distributing the product contained in pocket 10, is inserted inside nozzle 10. This pump 8 is represented in dotted line in FIG. 1. It will be described in details hereafter.

Casing 1, as well as the pump and the product contained therein are integral with a rigid support 2. This support essentially comprises a flat rectangular cartridge 20, having a small thickness. One end of this cartridge is provided with a bracket 21, in this case a small cartridge forming a right angle with the plane of cartridge 20.

Bracket 21 has a circular central aperture, preferably with an indented edge, in which the nozzle is inserted by resilient racheting thanks to the presence of distortable tabs 120.

At the other end, there is provided a pair of legs 22 which also extend at a right angle with the cartridge, on the same side thereof as bracket 21.

As can be understood when observing FIG. 1, casing 1 is maintained on support 2, both at the level of nozzle 11 by bracket 21 and at the level of pocket 10 which is fitted between the two legs 22 and thus maintained in a centered and immovable position in the transverse direction.

Cartridge 20 is provided with a pair of free rotating gears 23, 24 located near one another. They make up a counting means for the number of distributed doses; their disposition and operation is described in the already mentioned simultaneous Patent Application U.S. Ser. No. 08/097,635, filed Jul. 26, 1993, now U.S. Pat. No. 5,390,822. Their role is also to prevent further distribution when a determined number of doses has been distributed and when the vial is almost empty. To achieve that, they mutually block each other when this number is reached and it is then impossible to have them turn again.

Between pocket 10 and nozzle 11, casing 1 is provided with a front part 15 which has the general shape of a cylindrical sleeve and which surrounds a part of pump 8. The ZZ' axis of sleeve 15 is perpendicular to the YY' longitudinal general direction of the pocket and nozzle. Part 15 presents a flat face 150 (with a circular contour) on the side opposite to cartridge 20, said flat face being distortable in the ZZ' direction so that the pump can be actuated, as will be explained later.

As can be seen more in detail in FIG. 2, the body 80 of pump 8 presents two parts which define a right angle, which makes it have the general shape of a pipe. Reference 800 has been used to designate one of these parts—which corresponds to the tube of the pipe— and reference 801 has been used to designate the other part—which corresponds to the bowl of the pipe.

Part 800 has the shape of a revolution, with axis Y–Y' corresponding to the axis of the nozzle. This pan 800 is inserted into the nozzle. It has thus a truncated cone-like shoulder 86 capable of resiliently racheting itself into the wall of the nozzle. From this shoulder to the free end of pan 800, one finds a cylindrical part 82, of which the diameter decreases step-by-step until the truncated cone-like tip 81. Part 801 has a generally tubular outer wall, with axis Z–Z', which is coupled by radial blades 831 to a central tube 83. The latter has an annular sealing lip 830 at its free end. Part 800 is pierced with a diagonal channel 820, 830 which is bent at a right angle and whose uphill side 830 comes out inside tube 83 and whose downhill side 820 comes out outwardly by its end part 810, a little before the tip 81 (see FIG. 5). The pump furthermore includes a generally cylindrical part 85, including a closed end and an open end. The closed end consists of a socket 852 which is provided with a flat bottom 851, adapting to the tubular part 83 like a cylinder on a piston. The pan of the member 85 located on the open side is a sleeve coaxial with part 852, presenting longitudinal slits 851 permitting its engagement on pump body 80. Part 801 of the pump body has elements 84 serving as a stop for a compression spring 87, located inside pocket 10, and pulling member 85 to bring it into contact with the wall of pocket 10 in an easily distortable zone 15. Spring 87 can be made of a plastic material and can be moulded integral with member 85. The front face of member 85 rests against face 150 of sleeve 15. The presence of a bellows at this level is not a prerequisite given the flexibility of the wall of pocket 10 and given that its distortable feature is only necessary on a very small stroke (a few millimeters).

Figure 11:
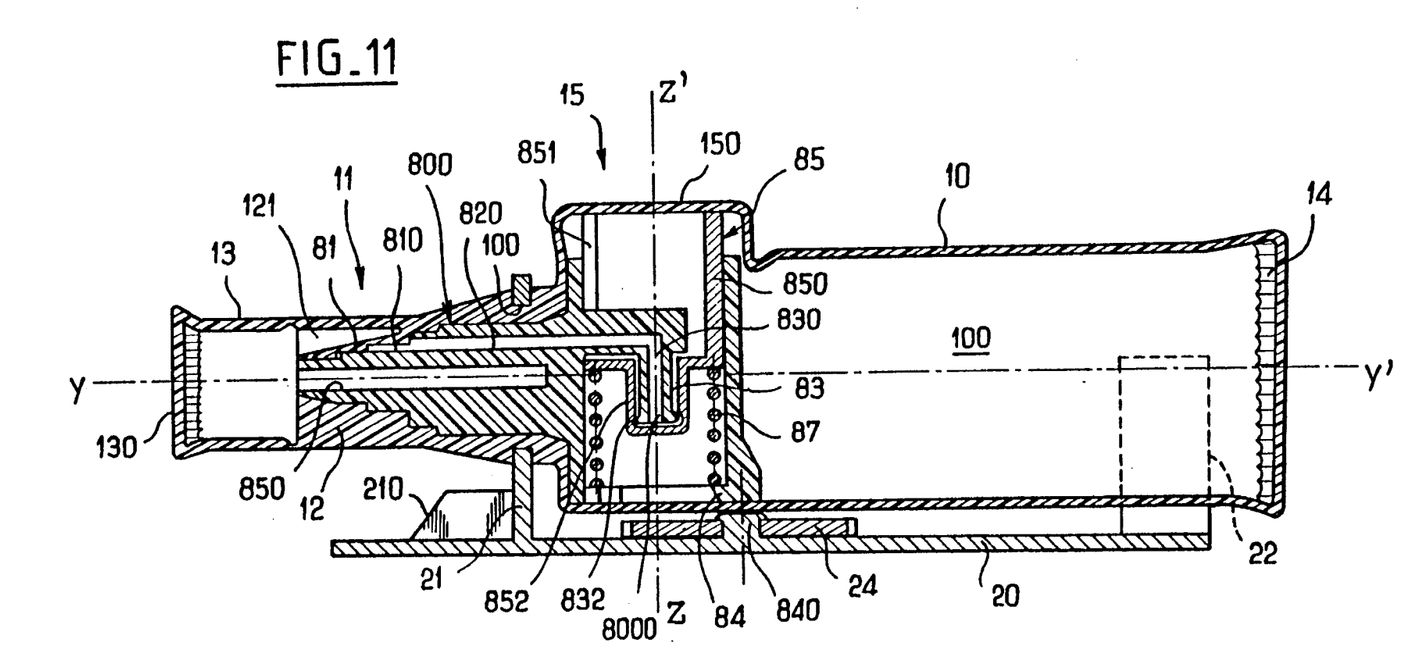
FIG. 11 is a cross sectional longitudinal view of the vial of FIG. 1.

By simply observing FIG. 11, it can be understood that by pressing on zone 150 according to the Z–Z' axis, member 85 is made to go down inside pocket 10 while compressing spring 87. This increases the volume in (variable volume) chamber 800 comprising bore 830 and the space at the bottom of socket 852.

Figure 17:
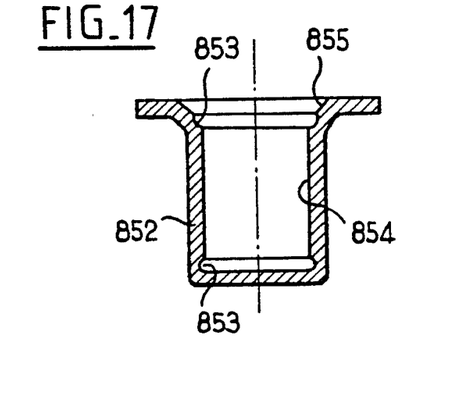
FIG. 17 is a large-scale cross-sectional axial detailed view of the socket which is part of the actuating member of the pump.
Figure 18:
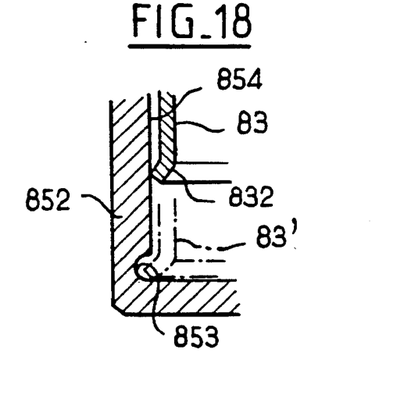
FIG. 18 is a detailed view showing the engagement of the pump piston against the wall of this socket.

As can be clearly seen in FIG. 17, the internal wall of socket 852 comprises a main cylindrical part surrounded, at the level of its higher and lower parts, with annular grooves 853 having a larger diameter. The upper groove itself is surrounded by an inlet chamfer 855 having a cone-shapped wall. This latter eases the centering of the free end of tube 83 when it goes down in the socket. The sealing lip 832 consists in an oblique, outwardly and downwardly oriented rim of the wall of tube 83. Thus when the lip is positioned opposite a groove 853, it is not compressed and allows the fluid product to flow freely from the outside toward the inside of tube 83 and vice versa. Such a position is illustrated FIG. 18, in which the tube is illustrated in dotted lines and is referenced 83'. Nevertheless, when lip 832 is positioned opposite the part of cylindrical wall 854, it is compressed and play the role of a seal, thus preventing the product to escape from the inside toward the outside of tube 83. Yet, in this position, represented in continuous lines in FIG. 18, the flowing of the product along wall 854 toward the inside of the tube remains possible thanks to the inside flexibility of the lip. The aspiration of the product contained in the casing, in chamber 8000 is thus possible but it must be expelled via central channel 830.

In the region 12 of the nozzle which surrounds this part 800, in the neighbourhood of aperture 810, a cavity 121 is provided which increases the flexibility and the distortability of the nozzle wall in a determined region, which enables the product to escape as a jet having a well-defined orientation in space.

Figure 3:
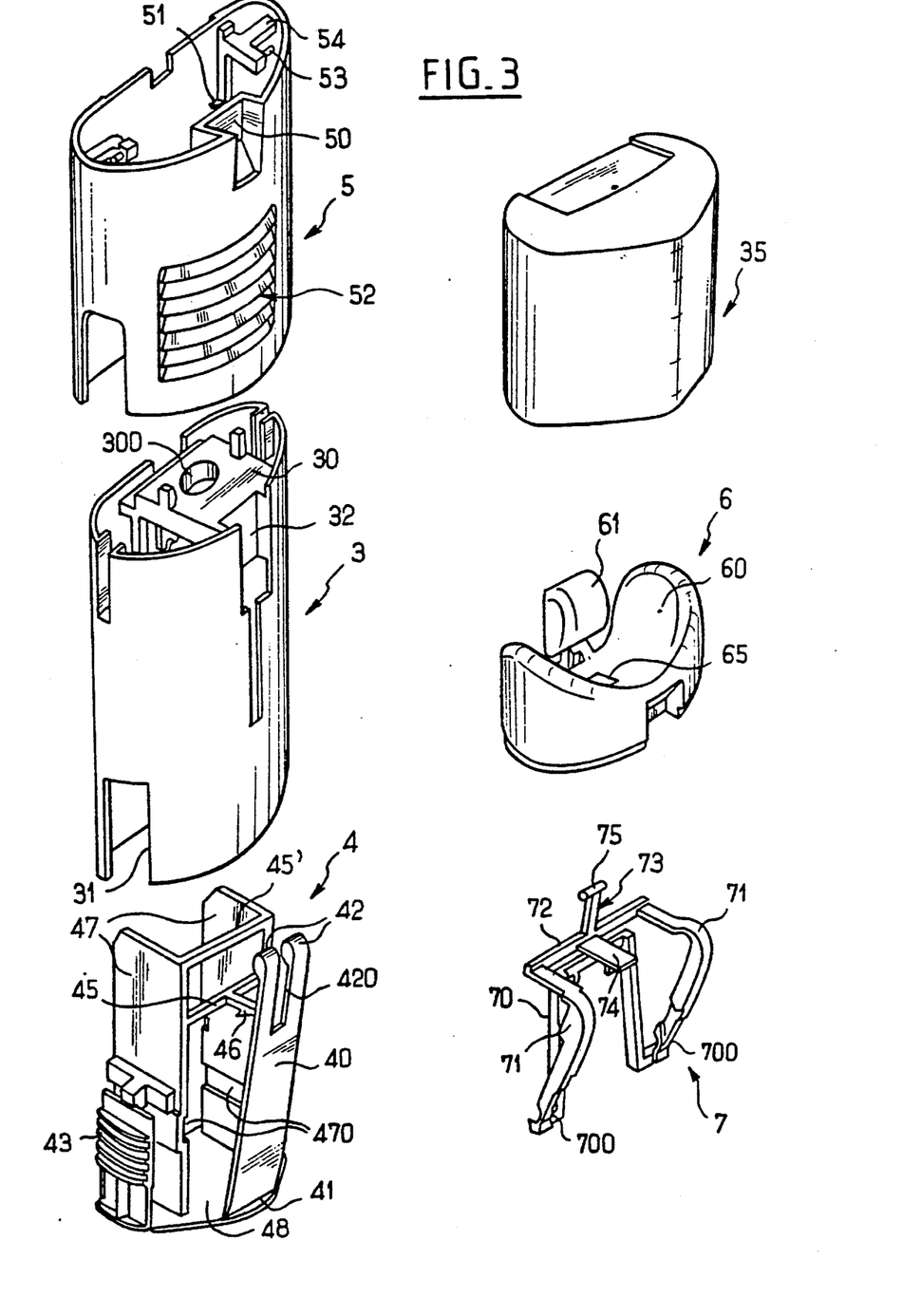
FIG. 3 is an exploded perspective view of the various elements which is part of the device.
Figure 4:
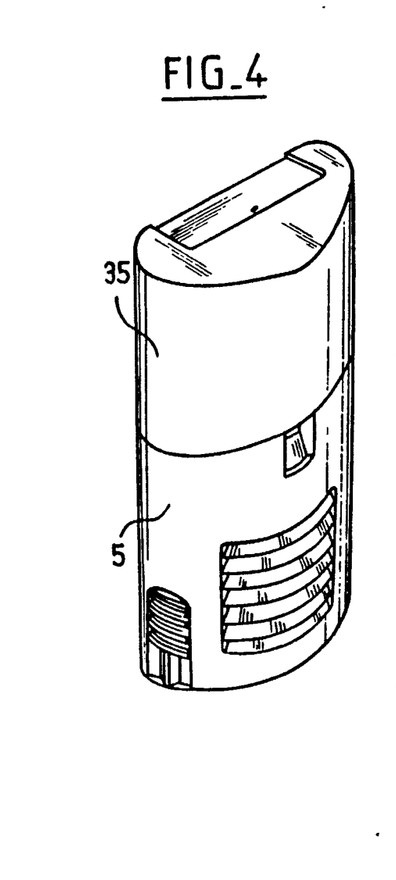
FIG. 4 is a perspective view of the device, in a closed state.

The device represented FIG. 3 comprises the six following elements, which are all made of plastic material:

a tubular body 3, the contour of which is adapted to the shape of the eye;

a drawer 4, which can be fitted in body 3;

a shell 5, which defines a plunger and which can be slidebly fitted, with a slight play, on body 3;

a fitting 6, made in a flexible material, which is to be glued on one of the ends of body 3;

a protecting lid 35 having the shape of a hood, which can be adapted on the end part of body 3 and which receives fitting 6, and which is adapted to cover this latter.

The dimensions of body 3 are sufficient to receive a vial of the type previously described. One of its ends is provided with a front wall 30 pierced with a central aperture 300 providing passage for nozzle 11 when the vial is placed in the device (see FIG. 5). Fitting 6 is glued against this wall 30.

Drawer 4 comprises two parallel and longitudinal cartridges 47 which are connected at one end via a bottom part 48, and at the other end by transverse small bars 45, 45'. One (45) of this small bars is provided with a small lever equipped with a locking nose 46. The base of the lever is connected to a small bar 45 by a less resistant area which plays the role of a hinge and authorizes a slight resilient deflection of the lever during pivoting.

Drawer 4 is equipped with a tab 40 which extends longitudinally above cartridges 47, in a plane which is perpendicular with these latter. Tab 40 is connected to the bottom part via a thinned area which is resiliently distortable. It can thus be flexed so as to come closer or to move away from cartridges 47. The free end of this tab has a rectangular central cut 420, the transverse rim (backward rim) of which is positioned opposite the locking nose 46. On both sides of cut 420, the free end of the tab displays an enlargement 42. The pair of enlargements 42 is positioned in such a way that it is located perpendicularly to the wall (having a circular cross-section) of the upper face of the member positioned in the device. Close to the backward end (on the side of bottom part 48) of the drawer, cartridges 47 display, on their internal wall, cavities (facings) 470 the position and dimensions of which enable the definition of housings for tabs 22, with which the support plate 20 of the vial is provided. Once these tabs have engaged in facings 470, plate 20 comes to rest against the longitudinal surfaces of cartridges 47, on the side opposite to tab 40.

On the sides of cartridges 47, them are side tabs 43 which make it easier to grasp the drawer 4 in view of its introduction (from backward to forward) and its placing by pushing, inside body 3. The vial can be delivered at the same time as the drawer, as will be explained later, by reference to FIG. 20 notably.

Side cavities 31 are provided in body 3 so as to receive legs 43 at the end of the pushing operation. These legs are advantageously provided with ridges (or other embossed patterns) which favour good grasping. The body 3 and drawer 4 are equipped with mutual blocking means such as resilient shoulder/cavity systems, which achieve a snap fit of the two elements at the end of the nesting operation and prevents there accidental uncoupling. Thus, to remove the drawer (notably when the vial is empty), a certain effort has to be exerted on it.

The body 3/drawer 4 unit makes up a receiving housing for the vial, in which this latter is protected and retained in view of the subsequent instillations of the eye lotion.

The flexible fitting has a main part 60 having a concave shape and an oblong contour, for instance oval, adapted to play the role of an eyepiece which can be correctly applied against the eyeball of a patient. This eyepiece is pierced with a central aperture 65 which is located opposite aperture 300 after the fitting has been glued against wall 30.

A part 61 for lowering the eyelid, which is an integral element of the flexible fitting 6 and which is located on the edge of part 60 and which is V-shape cut for this purpose in the central region of one of the elongated rims of the oblong contour. This part 612 is connected to part 60 via an area 612 having a small thickness and which defines an hinge and enables it to swing outwardly.

Figure 5:
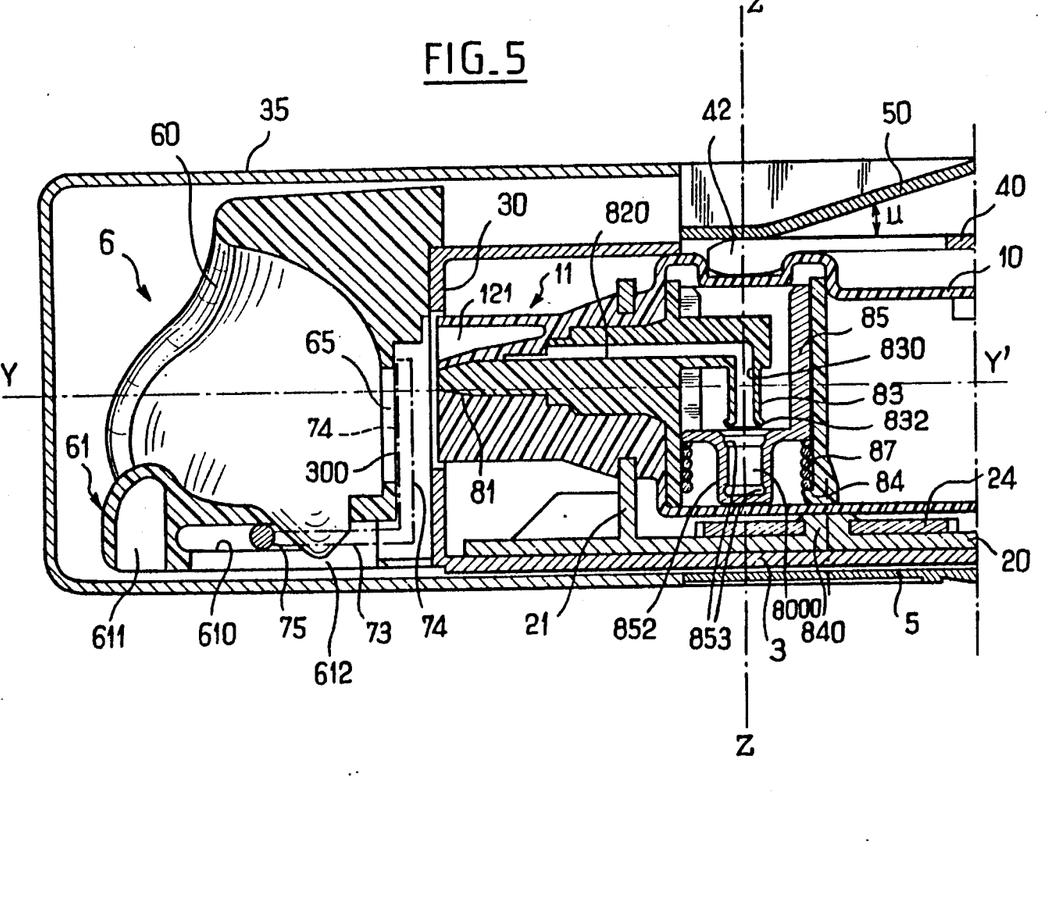
FIG. 5 is a partial cross sectional view of the end of the vial (on the nozzle side) hosed in the device of FIGS. 3 and 4.
Figure 6:
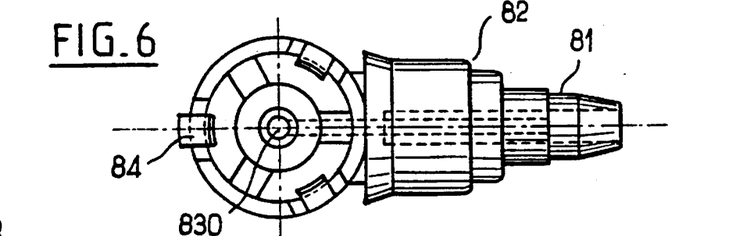
FIGS. 6, 7 and 8 are detailed views of the pump body, bottom, longitudinal and lateral views respectively.
Figure 7:
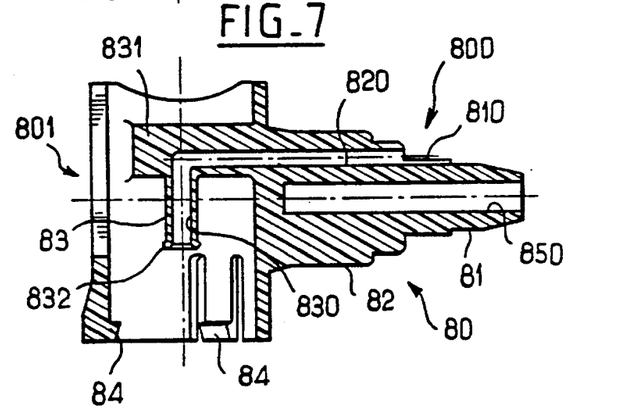
Figure 8:
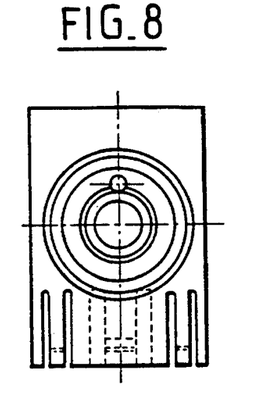

The eyelid lowering member 61 is provided with a curved wall, which can be best seen in FIG. 5, and which can rest against the lower eyelid of a patient so as to displace it by means of its outward pivoting, so that the cul-de-sac is well cleared for the instillation operation.

This element displays a cavity 611 in its lower face, which aims at making it lighter and more flexible. It also displays, on its lower part, a longitudinal T-shapped rib. The side ribs which correspond to the arms of the T are referenced 610 in the Figures.

The control device 7 is comprised with a fixed part (called the U bolt)—70—having the general shape of a U, the side arms of which extend longitudinally, said fixed pan being fitted with an articulated movable part. This articulated movable part comprises a pair of bent arms 71, which are similar and parallel to one another, and with are connected to one another at the level of one of their ends by a transverse small bar 72, and articulated at the level of their other end, by a less resistant region 700 (forming a hinge) which is located at the free end of the U bolt arms. Small bar 72 supports in its center, a T-shaped piece 73, the transverse arms of which are referenced 75, as well as a transverse cartridge 74.

Device 7 is configured in such a way that it can be placed in body 3, by inserting the end of body 3 beating wall 30. Appropriate cavities are provided in the internal wall of body 3 so as to receive and retain fixed part 70 therein. After device 7 has been nested, Fitting 6 can be adapted at the end part of body 3, in such a way that the transverse arms 75 of part 73 engage in ribs 610, and thereafter, the fitting is glued against front wall 30.

After the assembly, cartridge 74 (represented in mixed dotted lines in FIG. 5) comes to be positioned behind the eyepiece 60, against aperture 65 so as to obturate this latter. Of course, appropriate cavities provided in the back of fitting 6 enable the passage and pivoting of cartridge 74, which play the role of a shutter. As will be seen later, this shutter is retractable.

One at least of its main faces, shell 5 is provided with a set of ribs 52 (or other embossed patterns), which favour the grasping of the device and avoid its slipping from the fingers during use. It displays a recess of wall 50, defining a declined rail which comes in an opposite position as regards tab 40 of the drawer. Body 3 is provided with a cavity which is located opposite recess 50 so that the placing of shell 5 on body 3 is not disturbed. As an indication, rail 50 is an inclined plane which forms an angle—referenced u in FIG. 5—whose value is between 15° and 20°, for example 17.5°.

The configuration of shell 5 is such that it can nest with body 3 with a certain play. Its internal wall is provided with a finger 51 which actuates the counting means 23, 24 the vial is equipped with, and with a region 54 which operates the eyelid lowering member.

The configuration of lid 35 is such that it can nest on the end part of body 3, where it is maintained by friction. It thus comes to rest against shell 5 and covers fitting 6 (see FIG. 5).

Referring now to FIGS. 12 to 16, we are going to explain how to use the device which has just been described, for the instillation of an eye lotion.

For this operation, the tearaway part 13 of the vial nozzle is torn away and the vial is placed inside the housing made up by drawer 4 and body 3.

Figure 12:
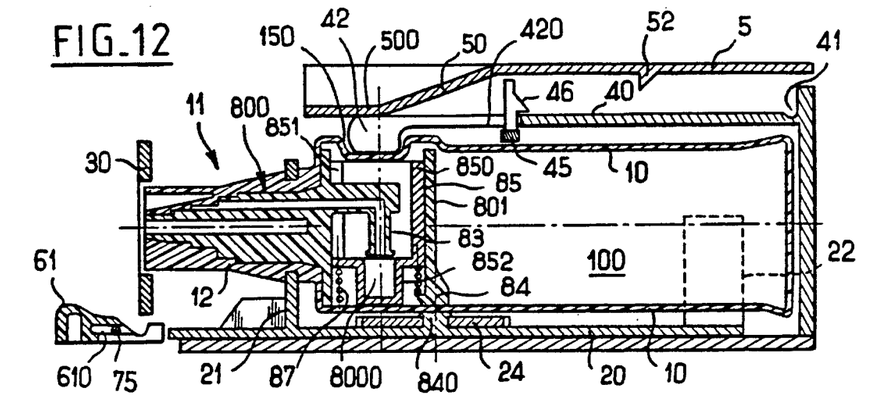
FIG. 12 is a similar view to that of FIG. 11, at a smaller scale, showing the vial housed inside the device of FIGS. 3 and 4, before the distribution of a dose of product.

At the beginning of the process, the actuating member 85 of the pump is supposed to be in its lower position as illustrated in FIG. 12. This lowering is achieved when the drawer/vial unit is placed in the body. The tubular piston 83 has thus come out of socket 852 and spring 87 is compressed at its maximum. This can be achieved because shell 5 which defines a plunger is at the end of its backward stroke on body 3. It is therefore the end part. 500 of rail 50 which is located opposite the free end of tab 40, so that this end is pushed downward. Protuberances 42 therefore press on the area 150 of the casing, pushing member 85 downward.

Furthermore, nose 46 is engaged against the backward rim of the indentation 420 provided in tab 40.

It should be noted that one member 84 for retaining spring 87 is located vertically above the axis 840 of one (24) of the counting gears. Thus, axis 840 absorbs a part of the pushing movement of this spring (via the wall of casing 10).

The eye lotion 100 which is contained in the casing 10 can penetrate freely, through slots 851 of the actuating member 85, in socket 852. Chamber 8000 then displays its maximum volume.

In this so-called "cocked" position, device 7 is not distorted and shows the configuration illustrated in FIG. 3. The eyelid lowering member 61 is in an inactive position almost in line with cartridge 20.

The eyepiece 60 is not illustrated in FIGS. 12 to 16 for the purpose of easy reading.

When the patient wants to use the device so as to instill drops of the eye lotion into his or her eyes, he or she first removes lid 35 so as to uncover the eyepiece. He or she then places the eyepiece against the eye in which the eye lotion is to be instilled; with the eyepiece resting against the eyeball, he or she then moves shell 5 toward his or her eye; for that purpose, he or she grasps the ribbed area 52 of the shell with his or her fingers. As the shell moves forward, as symbolized by arrow F1 in FIG. 13, the eyelid lowering member 61 pivots downwardly as illustrated by arrow F3 in this figure.

Figure 9:
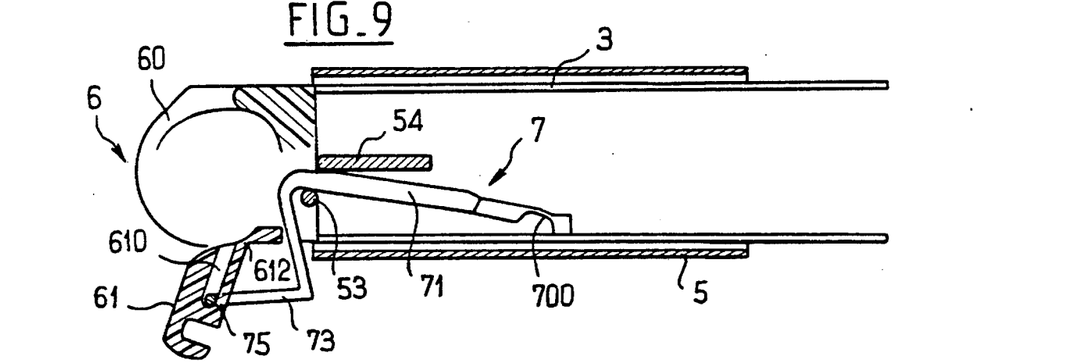
FIGS. 9 and 10 are cross sectional longitudinal schematic views of the device which illustrate the control principle for the swinging of the eyelid lowering member.
Figure 10:
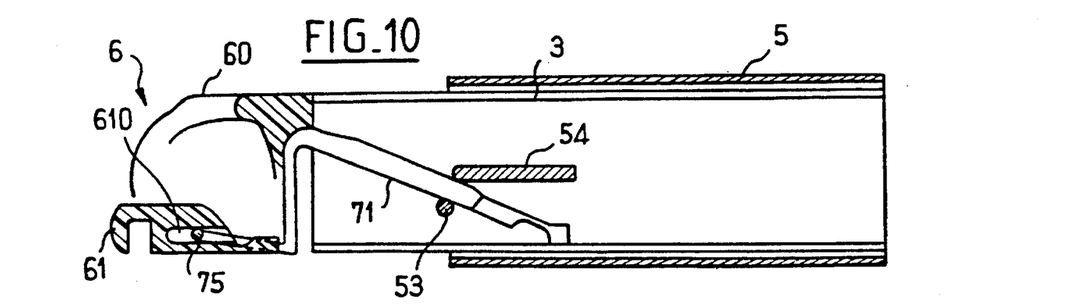

This movement is obtained thanks to the presence of actuating members 53, 54 inside shell 5, said actuating members being connected to the side bent arms 71 of device 7. Members 53 and 54 respectively control the upward and downward movement of the eyelid lowering member. This is illustrated in FIGS. 9 and 10. In FIG. 10, plunger 5 is in a backward position and device 7 shows its normal, non distorted configuration. The forward movement of plunger 5 forces bent levers 71, via the control members 53, 54, to deflect downwardly, which deflects member 61 around the hinge portion 612; at the same time, arms 75 are displaced in slides 70.

Of course, in case of reverse movement (in the backward direction) of the plunger 5, the eyelid lowering member 61 comes up again.

Figure 13:
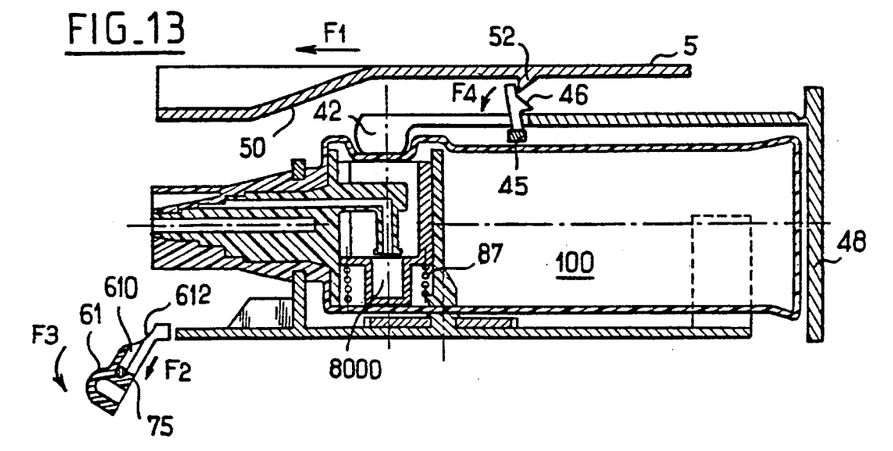
FIGS. 13, 14, 15 and 16 are partial or incomplete views, which correspond to FIG. 12 and illustrate the various stages of the product distribution process.

In FIG. 13, arrow F2 illustrates the movement of arm 75 in slides 610.

At the same time, following the lowering of the eyelid lowering member, shutter 74 (not shown in FIGS. 12 and 16) which is integral with is latter, is retracted, thus uncovering aperture 65 of the eyepiece.

When plunger 5 has finished its forward stroke, a stop 52 provided on the internal wall of this plunger, comes against the locking nose 46 and makes this latter pivot forward, has symbolized by arrow F4 in FIG. 13. Nose 46 is thus placed away from the back rim of slot 420 and frees tab 40. Tab 40 is therefore free to go up and, under the pressure of spring 87 contained in the pump, member 85 goes up, as symbolized by arrow G1 FIG. 14. Tab 40 pivots upwardly around the hinge-forming region 41, as symbolized by arrow G2.

The eye lotion which was contained inside socket 852, in the variable-volume chamber 8000, is therefore compresses inside this latter and forced out of the pump body through channels 830, 820. It comes out via aperture 810 and is expelled through opening 65 (which has previously been uncovered) of the eyepiece, according to a jet having a well defined orientation and represented FIG. 14, in the form of droplets 1000. These droplets end up in the eye cul-de-sac which has previously been exposed thanks to the eyelid lowering member.

Figure 14:
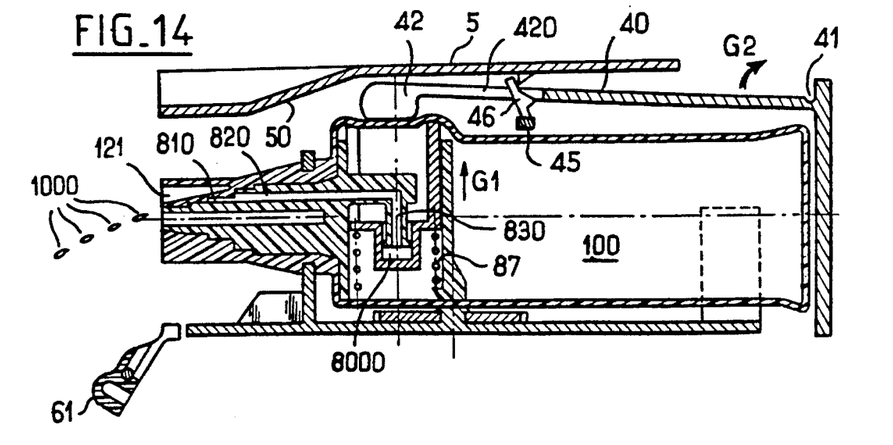
Figure 15:
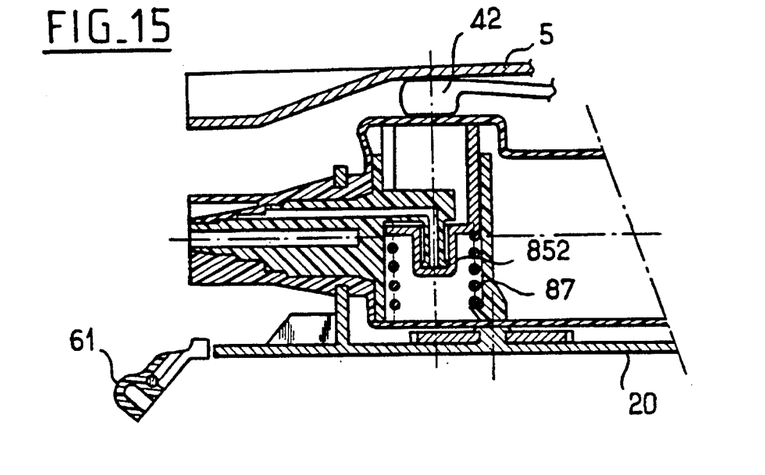

The expelled dose of product is of a well defined volume, which corresponds to the volume decrease in chamber 8000.

For each forward stoke of the plunger (the F1 direction), the plunger actuates the counting means 23–24 by means of the above-mentioned finger 51. When the counter is blocked, which means that the vial is almost empty, the patient can feel a resistance and an abnormal pressure,on his eyeball, which warns him about the situation.

Figure 16:
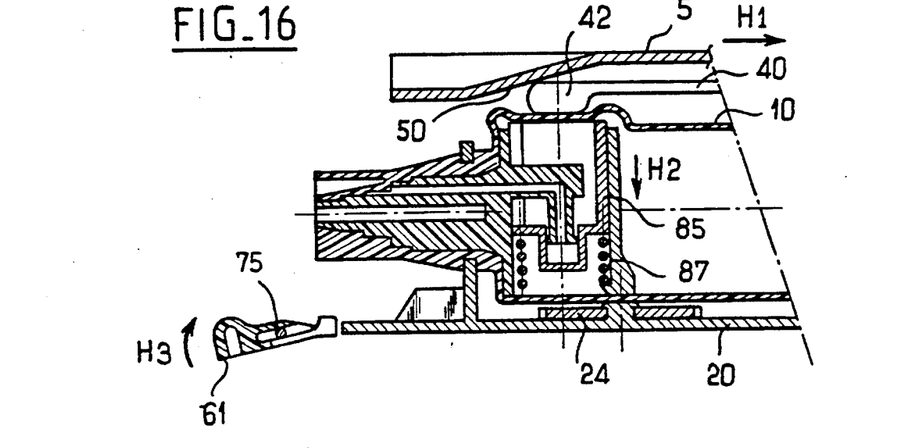

In order to re-cock the device after each instillation of one dose of product, one just has to move plunger 5 in the reverse direction, as illustrated in FIG. 16 and symbolized by arrow H1. The inclined rail 50 acts on the end of tab 40 so as to make it pivot downwardly, which effects a downward push on the actuating member 85 (arrow H2) via the protuberances 42 and through the wall of casing 10; this effects in compressing spring 87 again. At the same time, the eyelid lowering member 61 goes up (arrow H3).

It should be noted that this re-cocking operation can be carried out very easily and with a reduced effort. The operation can be carried out by placing the device on a table, with bottom part 48 of the housing placed on the table, and then lowering shell 5. When a small slope is selected for rail 50 (according to the plunger/pump ratio), spring 87 can be compressed more easily, even if it is rather powerful.

When it goes down, the backward rim of slot 420 pushes forward nose 46 momentarily, thanks to the fact that it is placed on an inclined plane. Then, at the end of the downward stroke of member 85, nose 46 automatically (thanks to its resilient nature) locks tab 40 in its low position.

The device is then cocked and ready for another use (for instance in the other eye). If instillation is not done immediately, the user puts lid 35 back in place and stores the vial-containing device until he must use it again. It should be noted that in storage position, the eyepiece is obturated by protecting shutter 74, which is particularly advantageous from an hygienic point of view.

The drop instillation operation using such a device is effected in a particularly soft manner as during this operation, the patient needs not overcome the action of spring 87. This latter is cocked by the user after instillation. The effort required to compress the spring is therefore not transmitted to the eye. This is particularly significant for unskilled or physically weak people, more particularly elderly people.

The wall of the device can advantageously be provided with one or two windows enabling .the user to read some information written on the vial, notably at the level of the counter (number of distributed doses or indication that the vial is almost empty), and regarding the nature of the eye lotion, thanks to an information label stock on the vial.

Figure 19:
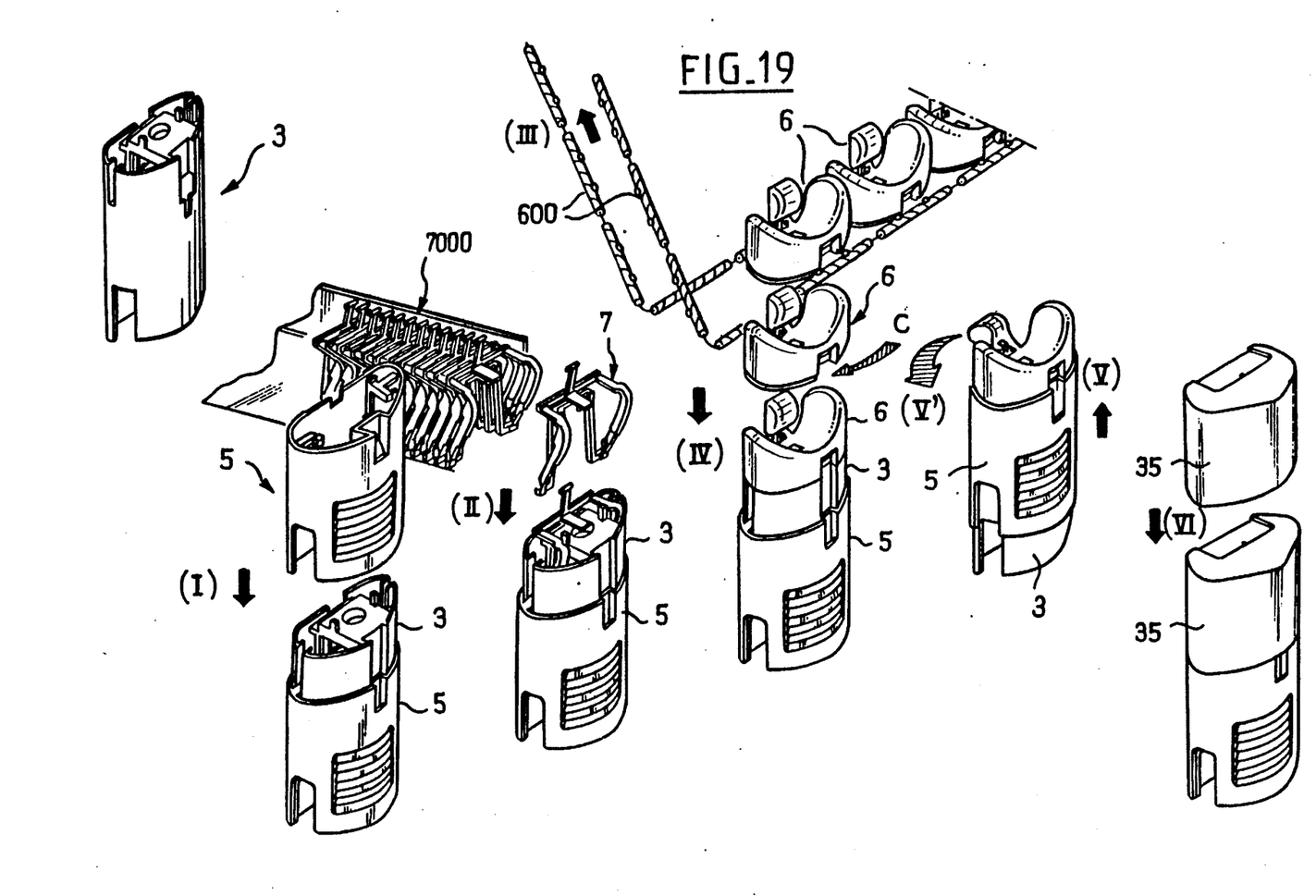
FIG. 19 is a schematic perspective view showing the various possible manufacturing stages of the device.

FIG. 19 shows the various stages of a possible manufacturing process of a device according to the invention. The various elements which make up the device are obtained by injection moulding. In a first stage (1) the shell is placed on the body (3). Devices 7 are stored in a magazine 7000, from which they are individually taken and then they are inserted in a body 3/shell 5 unit, as represented by stage (II). Fittings 6 are moulded in the form of a set strip of individual fittings connected by tearaway edges 600. At the gluing station for fittings 6, these latter are detached from the strip and tearaway edges continue their movement alone, as illustrated by arrow (III). Fitting 6 is then placed and glued on body 3, as symbolized by arrow C.

During the following stage (V), the eyelid lowering member is tested, so as to know if the fitting has been assembled correctly. To achieve that, plunger 5 is moved on body 3 and the correct pivoting of the eyelid lowering member is checked, as symbolized by arrow (V').

The lid is then placed on the unit, as symbolized by arrow (VI).

The device can then be sold as such, i.e. without the drawer 4, said drawer being sold separately with an eye lotion vial.

FIG. 20 is a precise illustration of the (VII) insertion stage of a vial in a drawer. Preferably, the back part of cartridge 20 is provided with an indication, for example a label 200 which indicates the features of the eye lotion and the indications concerning its manufacturing.

Once the vial has been introduced in the drawer 4, the unit is protected in a plastic transparent film in which it is protected from moisture (stage(VIII)). This packaging mode is interesting because casing 1 which is rather fragile, is perfectly protected from any kind of aggression as it is altogether protected by the support plate 20 and by the side plates 47 of the drawer.

Thus, when a patient wants to place a new vial in his device, he just needs tear the plastic film and take the drawer 4 and the eye lotion vial, remove the tearaway part 13 of the vial nozzle, and then introduce the drawer and its vial in the device. The operation is quite easy. When the vial is empty, it is discarded with the drawer.

It shall be understood that it is also possible to sell complete devices (including the drawer) and vials alone. The patient then has to place the vial in the drawer, and the drawer/vial unit in the device.

The invention can also be applied to a vial comprising two pumps placed next to one another and distribution one product each, both products mixing together at the outlet (which is of interest, notably when dealing with a non stable mixture).

What is claimed is:

1. A packaging vial for dispensing in calibrated successive doses a fluid medicinal product comprising:

a flexible casing containing the product, being free from air, comprising a pocket having a thin and deformable wall, and having a tubular nozzle connected to said casing for discharging the product;

a pump including a fixed body inserted into said nozzle and a moveable actuating member disposed inside said casing and displaced through said thin and deformable wall of said casing, said fixed body including a chamber wherein movement of said actuating member in a first direction draws the product into said chamber while movement of said actuating member in an opposite second direction discharges a calibrated dose of the product from the chamber;

a receiving housing; and a pushing means for pushing said actuating member, said pushing means being moveable in a direction perpendicular with the axis of the nozzle, and further being supported by an articulated tab integral with said housing, and further having a plunger being graspable by the user.

2. The packaging vial as defined in claim 1 in which the plunger is integral with a finger for actuating a counting means.

* * * * *